Figure 1:
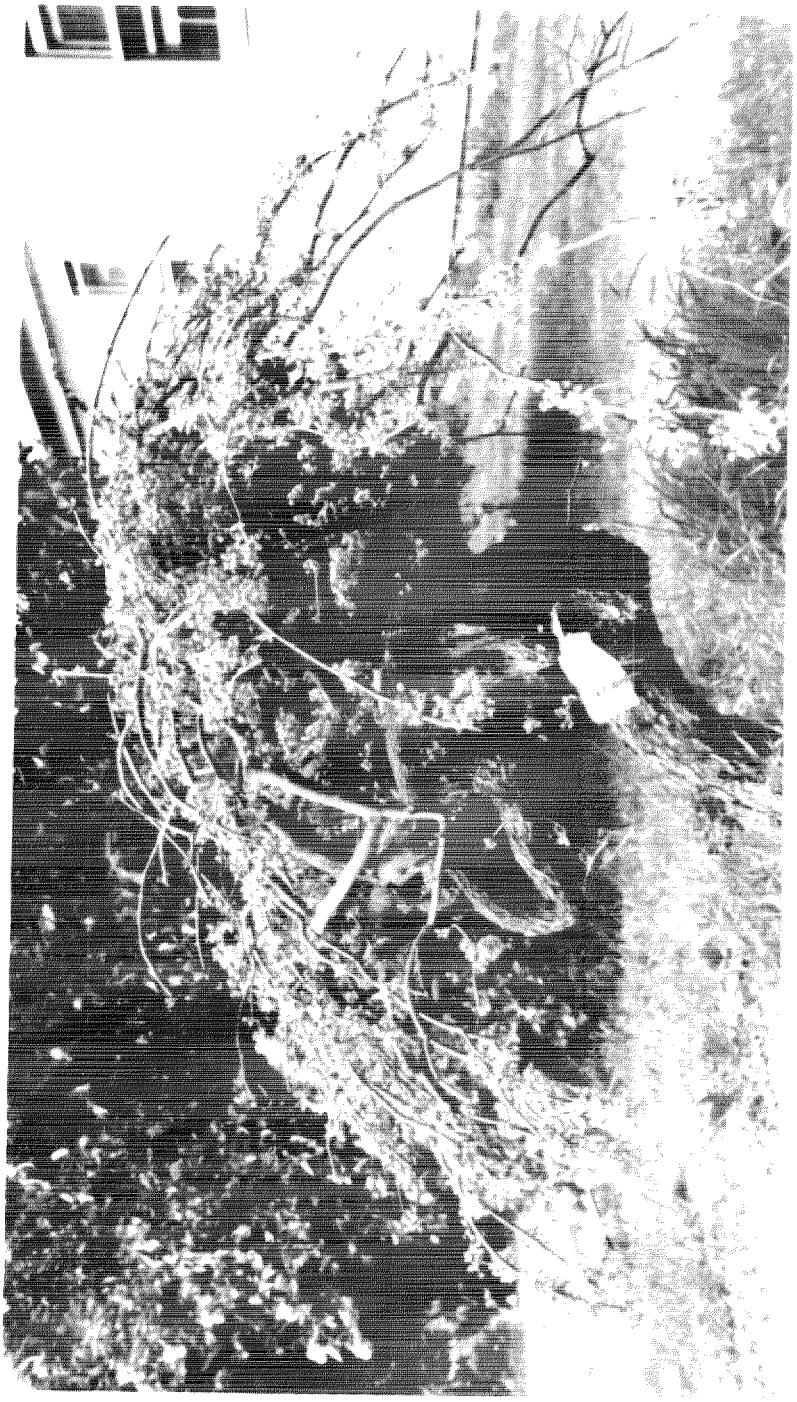

US00PP10328P

United States Patent [19]

Covey

[11] Patent Number: Plant 10,328

[45] Date of Patent: Apr. 14, 1998

[54] EASTERN REDBUD TREE NAMED 'COVEY'

[75] Inventor: Cornelia L. Covey, Westfield, N.Y.

[73] Assignee: Brotzman's Nursery, Inc., Madison, Ohio

[21] Appl. No.: 622,055

[22] Filed: Mar. 27, 1996

[51] Int. Cl.[6] ..... A01H 5/00

[52] U.S. Cl. ..... Plt./51.1

[58] Field of Search ..... Plt./51.1

[56] References Cited

U.S. PATENT DOCUMENTS

P.P. 8,640 3/1994 Hosage ..... Plt./51.1

OTHER PUBLICATIONS

Little, Jr., 1953, Checklist of Native and Naturalized Trees of the United States (Including Alaska) Agriculture Handbook No. 41, pp. 10–11, 102–103.

*Primary Examiner*—Howard J. Locker

*Attorney, Agent, or Firm*—Renner, Otto, Boisselle & Sklar, P.L.L.

[57] ABSTRACT

An eastern redbud plant named Covey, distinguished by its contorted stems and pendulous branchlets, light green new growth, large heart shaped leaves with pointed tips, dull finish and papery texture and scaly mature bark with reddish underlay, which make it a novel and striking specimen for landscape use. An additional asset is its winter hardiness to at least −23° F. (minus twenty-three degrees Fahrenheit), making it suitable for use in northern climates.

2 Drawing Sheets

This invention relates to a new and distinct variety of eastern redbud, botanically known as *Cercis canadensis* var. *canadensis*, and known by the cultivar named Covey.

This new cultivar originated as a seedling growing at a private residence in Westfield, N.Y., and which has been vegetatively propagated at Brotzman's Nursery, Inc. in Madison, Ohio. As it matured, this plant was noted as distinctive because of its contorted stems and major branches and its lack of an upright leader shoot, all shoots instead arching over to provide pendulous branchlets that give an umbrella-shaped crown.

The Covey variety is the only variant of eastern redbud of which I am aware that displays such a "weeping" habit. There is a patented weeping variety of the Texas Redbud (*Cercis canadensis* var. *texensis*) (U.S. Plant Pat. No. 8,640), 'Traveller', from which Covey differs in its light green new growth and larger heart shaped leaves with pointed tips, dull finish and papery texture, dark brown and scaly mature bark with reddish underlay. An additional asset of Covey is its winter hardiness to at least −23° F., making it suitable for use in northern climates.

In the covey variety, new shots typically originate from the mid to basal portion of the previous year's shoots, rather than from the tips. Considerable crossing of the zig-zag stems occurs within the crown of the plant. As a result, the crown becomes very densely branched, which is particularly noticeable in the summer when the leaves overlap like shingles on a roof. One side effect of this density is that some shoots in the interior of the crown die from lack of sufficient light and must be removed in the course of routine maintenance.

The original plant of this new variety, which is over 30 years old, is approximately 1.5 meters tall and 2.5 meters wide at its widest dimension, and its main stem is approximately 20 cm. in diameter. However, its growth was suppressed for a number or years by competition from an adjacent shrub. Vegetative offspring of this plant have been "trained" to a more upright form by tying the main stem to a stake, up to a height of 2 meters or more, the pendulous crown developing above the uppermost support.

The Covey variety is vegetatively propagated by grafting, and plants propagated by this method consistently and uniformly display the unique characteristics of the original plant.

Figure 2:
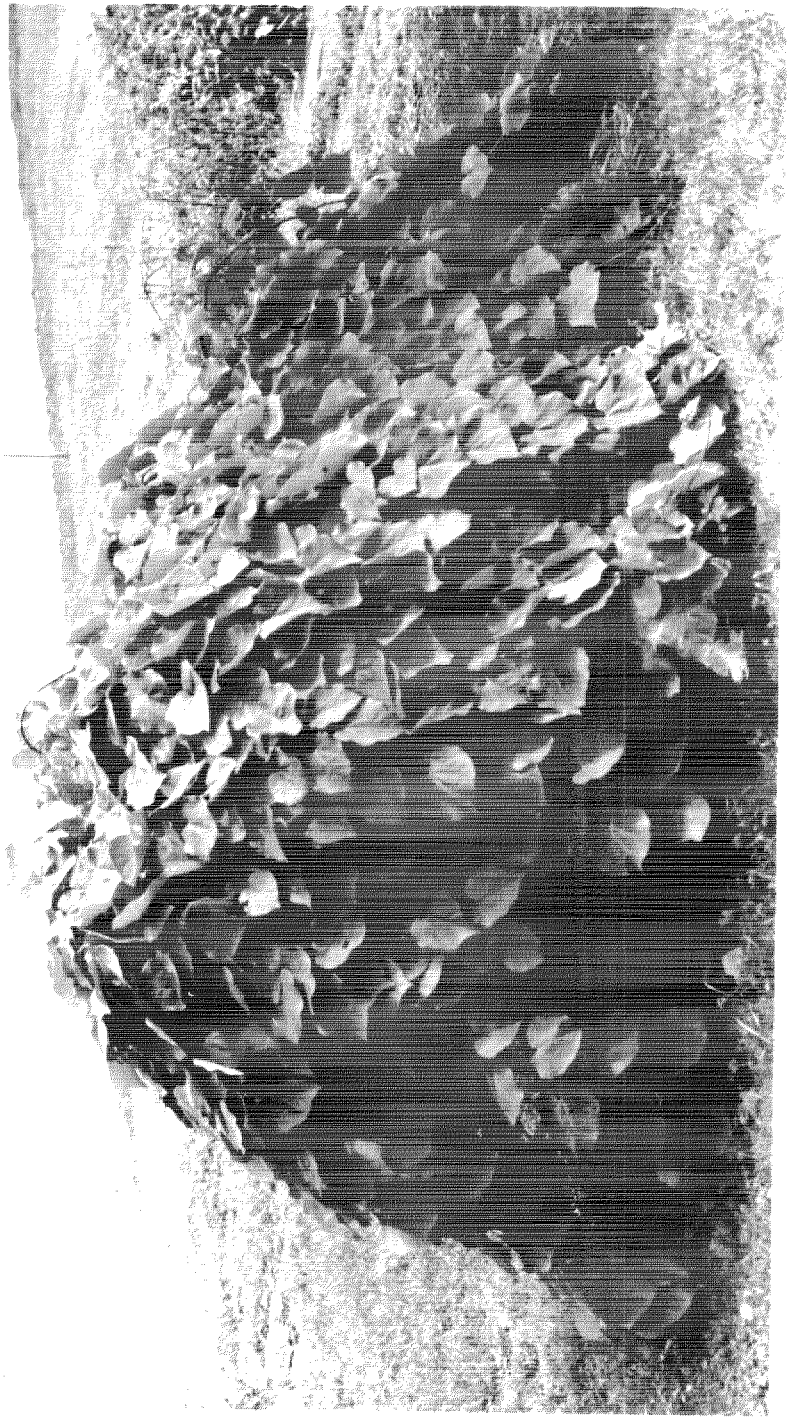

Referring now to the accompanying drawings:

FIG. 1 is a colored photograph illustrating in perspective view the overall appearance of the cultivar Covey in springt during flowering; and FIG. 2 is a colored photograph illustrating in perspective view the overall appearance of the cultivar Covey in full leaf during the summer months.

Both drawing figures show the colors as truly as is reasonably possible to obtain in colored reproduction of this type.

The following is a detailed description of my new cultivar Covey. Where color is different from the typical and is considered a distinguishing feature of this variety, where possible reference is made to specific colors on the chart issued by The Royal Horticultural Society, London, England. Here follows a detailed description of the characteristics of this variety, as displayed by specimens grown at Madison, Lake County, Ohio. Other than in features peculiar to its unique growth habit and somewhat larger than average leaves, it should be considered identical to traits typically exhibited by *C. canadensis* var. *canadensis*.

BOTANICAL DESCRIPTION

Parentage: Unknown — obtained as a seedling growing at a private residence in Westfield, N.Y.

Form/Size: When left untrained, it becomes a large mounded shrub/small tree (1.5 meters tall×2.5 meters wide) at maturity with contorted stem and primary branches, the smaller branches arching over to produce an umbrella or mushroom-shaped crown. In leaf, the plant appears as a mound of overlapping foliage. When properly supported and trained, it can be grown as a small tree to an undetermined height but probably not exceeding the 12–14 meters typical of var. *canadensis*.

Hardiness: Hardy in USDA Hardiness Zone 5. Was not injured after exposure to −23° F. (minus twenty-three degrees Fahrenheit) in January, 1994.

Growth rate: Moderate to rapid. 2 to 3-year old plants in the nursery produce 45 to 90 cm. of new growth in one year. The annual height increase is much less than this unless a leader is staked. In 1995, a non-irrigated 3-year old plant produced over 200 cm. of new leader growth and 100 cm. of lateral growth.

Stems: Dark brown to dark gray-brown, smooth, becoming scaly with age, revealing reddish color underneath; contorted.

Branches: 2-year branches are slender, dark brown to dark-gray brown with few lenticels. Current seasons's growth has internodal length of 3–6 cm. on dark brown to dark gray-brown strongly arching shoots, with abundant, slightly angled lenticels. All shoots and branches are very pendulous but due to the lack of apical dominance, new growth often reverses itself 180° (one hundred eighty degrees) from the direction of growth made the preceding year. Occasionally, the final growth of the season is tipped with chocolate-green bark, but usually dark brown. This dark color shows a tendency for early ripening (maturation) in the autumn, which is not a characteristic of var. *taxensis* when growing in northern states. Wood is white and the pith is tan.

Leaves: Deciduous, cordate with entire margins and tapering acute tips, leafstalks 3–6 cm. long. Mature leaf blades are 7–10 cm. long by 8–12 cm. wide, chartaceous, glabrous, dark blue green and dull on the upper surface, sparsely hairy and lighter below. New growth is light green, tinted red, becoming light green (Yellow-Green Group 144A) above and below. Fall color is yellow. Young, vigorous plants have produced leaves 13 cm. long by 22 cm. wide.

Flowers: Pea-like, 1.3 cm. long, in clusters 4–8 on older branches.

*Color.*—Purple Group 78B, appearing in early to mid May in Lake County, Ohio, lasting 2–3 weeks. Calyx color is Red-Purple Group 71B.

*Quantity.*—abundant. Fragrance: none.

Fruits: Flattened pods 5–10 cm. long×10–13 mm. wide, reddish brown, pendent.

I claim:

1. An eastern redbud plant named Covey, as described and illustrated, a small tree characterized by its contorted stems and pendulous branchlets, light green new growth, large heart shaped leaves with pointed tips, dull finish and papery texture, dark brown and scaly mature bark with reddish underlay, and winter hardiness.

* * * * *